US008105768B2

(12) United States Patent
Morrison et al.

(10) Patent No.: US 8,105,768 B2
(45) Date of Patent: Jan. 31, 2012

(54) METHODS OF IDENTIFYING PATIENTS FOR TREATMENT WITH HER-2/NEU INHIBITORS BASED ON DETECTION OF HER-2/NEU AND TOP2A GENE COPY NUMBER

(75) Inventors: Larry E. Morrison, Glen Ellyn, IL (US); Susan Jewell, Gurnee, IL (US); John S. Coon, Oak Park, IL (US)

(73) Assignees: Abbott Laboratories, Abbott Park, IL (US); Rush University Medical Center, Chicago, IL (US)

(*) Notice: Subject to any disclaimer, the term of this patent is extended or adjusted under 35 U.S.C. 154(b) by 0 days.

(21) Appl. No.: 11/371,294

(22) Filed: Mar. 8, 2006

(65) Prior Publication Data

US 2007/0161008 A1    Jul. 12, 2007

Related U.S. Application Data

(60) Provisional application No. 60/659,961, filed on Mar. 9, 2005.

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| 6,942,970 B2 * | 9/2005 | Isola et al. .................. 435/6 |
| 2002/0031515 A1 | 3/2002 | Caligiuri et al. |
| 2003/0134279 A1 | 7/2003 | Isola et al. |

FOREIGN PATENT DOCUMENTS

| WO | WO 02/066685 A | 8/2002 |
| WO | WO 02/066685 A1 | 8/2002 |
| WO | 03025127 A2 | 3/2003 |

OTHER PUBLICATIONS

Järvinen and Liu (Breast Cancer Research and Treatment, 2003, 78:299-311).*
Bofin et al (Cytopathology, 2003, 14:314-319).*
Vysis LSI® TOP2A/CEP® 17 Probe Mixture product description, 2 pages.*
Vogel et al (J of Clinical Oncology, 2002, 20:719-726).*
Jarvinen and Liu (Combinatorial Chemistry & High Throughput Screening, 2003, 6:455-470).*
Abbott Molecular PathVysion® Product Description for HER-2 DNA Probe Kit, 6 pages.*
Tockman et al (Cancer Res., 1992, 52:2711s-2718s).*
Feldman et al (Clinical Pharmacology & Therapeutics, 2007, 81:887-892).*
Nahta et al (Nature Clinical Practice Oncology, May 2006, 3:269-280).*
Stancovski et al (PNAS 1991, 88:8691-8695).*
Gordon et al (J Clinical Oncology, 2006, 24:4324-4332).*
Herbst et al (Clinical Cancer Research 2007, 13:6175-6181).*
Slamon D.J. et al.: "Use of Chemotherapy Plus a Monoclonal Antibody Against Her2 for Metastatic Breast Cancer that Overexpresses Her2", New England Journal of Medicine, The Massachusetts Medical Society, Waltham, MA, US, vol. 344, No. 11, Mar. 15, 2001, pp. 783-792.
Albanell J. et al.: "Tratuzumab, A Humanized Anti-Her2 Monoclonal Antibody, for the Treatment of Breast Cancer" Drugs of Today/ Medicamentos De Actualidad, J.R. Prous SS.A. International Publishers, ES, vol. 35, No. 12, 1999, pp. 931-946.
Levine M.: "Epirubicin in Breast Cancer: Present and Future", Clinical Breast Cancer, vol. 1, No. Suppl 1, Sep. 2000, pp. S62-S67.
Slamon, DJ, Use of Chemotherapy Plus a Monoclonal Antibody Against Her2 for Metastatic Breast Cancer That Overexpresses Her2, 2001, New England Journal of Medicine, vol. 344, No. 11, Mar. 15, 2001, pp. 783-792.
Albanell, J, Tratuzumab, A Humanized Anti-Her2 Monoclonal Antibody for the Treatment of Breast Cancer, 1999, Drugs of Today/ Medicamentos De Actualidad, vol. 35, No. 12, 1999, pp. 931-946.
Levine, M, Epirubicin in Breast Cancer: Present and Future, Clinical Breast Cancer, vol. 1, No. Suppl 1, Sep. 2000, pp. S62-S67.
V. Durbecq et al., Breast Cancer Research and Treatment, 77: 199-204 (2003).
Tero A.H. Jarvinen et al., Current Cancer Drug Targets, 6, 579-602 (2006).
Angelo Di Leo et al., Clinical Cancer Research, vol. 8, 1107-1116 (May 2002).
Aman U. Buzdar, et al., Journal of Clinical Oncology, vol. 24, No. 16, 2409-2411 (Jun. 1, 2006).
K. Park et al., European Journal of Cancer 39, 631-634 (2003).
Edurne Arriola et al., European Journal of Cancer 42, 2954-2960 (2006).
Ann S. Knoop et al., Journal of Clinical Oncology, vol. 23, No. 30, 7483-7490 (Oct. 20, 2005).
Minna Tanner, et al., Journal of Clinical Oncology, vol. 24, No. 16 (Jun. 1, 2006).
Jules Bordet Institute et al., Clinicaltrials.Gov, Identifier: NCT00162812 (Sep. 2005).
"Human Genome U95 Set", Internet Citation, Oct. 2, 2001, URL:http://www.affymetrix.com (1 page).

(Continued)

*Primary Examiner* — Laura B Goddard
(74) *Attorney, Agent, or Firm* — Pierce Atwood, LLP; Kevin M. Farrell, Esq.; David Wilson, Esq.

(57) ABSTRACT

The present invention provides methods for identifying cancer patients susceptible to effective treatment with trastuzumab and other medications that function similarly to trastuzumab. The invention is based on the discovery that certain chromosomal abnormalities can be used to selectively identify cancer patients that are likely to be successfully treated with medication that inhibits the signaling capability of the HER-2 receptor protein or otherwise function similarly to trastuzumab. The invention is based on the use of nucleic acid technology where nucleic acid probes are allowed to hybridize to cell samples and the number of copies of particular genetic regions quantified. The present invention also provides kits and sets of probes for use in identifying cancer patients susceptible to effective treatment with trastuzumab and other medications that function similarly to trastuzumab.

4 Claims, No Drawings

OTHER PUBLICATIONS

"Genechip Human Genome U133 Set", Internet Citation, Feb. 26, 2003, URL:http://affymetrix.com/support/techincal/batasheets/hgu133_datasheet.pdf (2 pages).

Constantine L et al: "Use of GeneChip high-density oligonucleotide arrays for gene monitoring", Life Science News, Amersham Life Science, US, Jan. 1, 1998 pp. 11-14, XP002964122, ISSN: 0969-0190 (4 pages).

Hansel, et al., "A Subset of Pancreatic Adenocarcinomas Demonstrates Coamplification of Topoisomerase IIx and HER2/neu—Use of Immunolabeling and Multicolor FISH for Potential Patient Screening and Treatment", American Society for Clinical Pathology, 2005, pp. 28-35 (8 pages).

Heselmeyer-Haddad, et al., "Detection of Chromosomal Aneuploidies and Gene Copy Number Changes in Fine Needle Aspirates is a Specific, Sensitive, and Objective Genetic Test for the Diagnosis of Breast Cancer", American Association for Cancer Research, 2002, pp. 2365-2369 (5 pages).

Chu, et al., "The Dual ErbB1/ErbB2 Inhibitor, Lapatinib (GW572016), Cooperates with Tamoxifen to Inhibit Both Cell Proliferation and Estrogen-Dependent Gene Expression in Antiestrogen-Resistant Breast Cancer", American Association for Cancer Research, 2005, Cover page with pp. 18-25 (9 pages).

* cited by examiner

METHODS OF IDENTIFYING PATIENTS FOR TREATMENT WITH HER-2/NEU INHIBITORS BASED ON DETECTION OF HER-2/NEU AND TOP2A GENE COPY NUMBER

This application claims priority to provisional application No. 60/659,961, filed on Mar. 9, 2005.

BACKGROUND OF THE INVENTION

Breast cancer is the most common female malignancy in most industrialized countries, as it is estimated to affect about 10% of the female population during their lifespan. Although its mortality has not increased along with its incidence, due to earlier diagnosis and improved treatment, it is still one of the predominant causes of death in middle-aged women.

The primary treatment for breast cancer is surgery, either alone or combined with systemic adjuvant therapy (hormonal or cytotoxic) and/or post-operative irradiation. Most patients are cured with these treatments, but approximately 25-30% of women with node-negative disease and at least 50-60% of women with positive nodes, who appear to be disease-free after locoregional treatment, will relapse and need treatment for their metastatic disease. Thus, metastatic breast cancer is a significant and growing problem in oncology.

Approximately 30 to 40% of women with operable breast cancer eventually develop distant metastases. Metastatic breast cancer is commonly treated with anthracyclines, such as doxorubicin and epirubicin, which act via inhibiting the topoisomerase II (TOP2A) enzyme in cancer cells. A favorable response to TOP2A inhibitor-based chemotherapy improves post-chemotherapy survival and has a positive effect on the quality of life.

The response of patients to topoisomerase II inhibitors is widely variable. In addition, only 5 to 10% of breast cancer patients with overtly metastatic disease achieve complete clinical remission. In 30 to 50% of such cases, the response is partial, and the duration of response typically ranges from 6 to 24 months. In the remaining patients, either no objective response is detected, or the disease progresses despite ongoing treatment.

Overexpression of the HER-2 receptor protein (ERBB2) has long been associated with more aggressive breast cancer and results primarily from amplification of the gene HER-2/neu, also referred to as ERBB2 or more simply as HER-2. More importantly, HER-2 amplification is an established predictor of tumor response to the humanized anti-ERBB2 antibody trastuzumab (sold commercially as Herceptin® by Genentech). However, breast carcinomas lacking HER-2 amplification rarely respond to trastuzumab while 20-40% of tumors with HER-2 amplification have good response. Moreover, trastuzumab has cardiotoxic side effects and is expensive. Thus, there is a need for methods for identifying those tumors that can be treated more successfully with trastuzumab. Such methods will enable physicians to better match trastuzumab therapy with patients more likely to benefit from such therapy, thereby avoiding prescription of trastuzumab therapy for patients unlikely to benefit from trastuzumab and further avoiding the attendant patient morbidity and cost of doing so.

It has been suggested that candidates for effective treatment with TOP2A inhibitors can be identified by detecting the copy numbers for HER-2/neu and TOP2A. U.S. 2003/0134279A1 by Isola, et al. Patients indicating amplification of both HER-2/neu and TOP2A are said to be good candidates for treatment with TOP2A inhibitors.

SUMMARY OF THE INVENTION

The present invention provides methods for identifying cancer patients susceptible to effective treatment with trastuzumab and other medications that function similarly to trastuzumab. It is believed that trastuzumab functions, in part, by inhibiting the signal capability of the HER-2 receptor protein. Thus, the invention provides methods for determining the susceptibility of cancer patients to successful treatment with medication that inhibits the signaling capability of the HER-2 receptor protein. The invention is based on the discovery that certain chromosomal abnormalities can be used to selectively identify cancer patients that are likely to be successfully treated with medication that inhibits the signaling capability of the HER-2 receptor protein or otherwise function similarly to trastuzumab. The invention is based on the use of nucleic acid technology where nucleic acid probes are allowed to hybridize to cell samples and the number of copies of particular genetic regions quantified. Preferably, in situ hybridization and, more preferably, fluorescent in situ hybridization (FISH) with fluorescently labeled nucleic acid probes is used. The hybridization results are then used to determine the likelihood that the patient will be treated successfully with medication that inhibits the signaling capability of the HER-2 receptor protein. Preferably, the cell samples are breast cell samples and the medication is trastuzumab or a medication that functions similarly to trastuzumab.

The methods for identifying candidate patients for treatment with medication that inhibits the signaling capability of the HER-2 receptor protein comprise: a) obtaining a biological sample comprising cells from a patient suspected of having a carcinoma; b) contacting the sample with a set of chromosomal probes, under hybridization conditions, wherein the probes are able to detect copy numbers for chromosomal regions near or including HER-2/neu and one or more of the approximate genetic loci for TOP2A, the q arm of chromosome 1 (1q) and chromosome 10 in the cells; and c) identifying the candidate as being suitable for treatment, wherein the identification comprises demonstrating amplification of the copy number for HER-2/neu and abnormality of the one or more other markers. Typically, probes to 1q extend approximately equidistant from the locus 1q25 to approximately the PTGS2 gene (1q31) on the q arm or to any of the genetic loci within that distance. It is believed that some genes just telomeric to the PTGS2 gene are effective markers and are included in the 1q locus. Preferably, the probes are directed to the 1q25 locus, the PTGS2 gene or to any other locus within the 1q region specified above. The candidate patient may only be suspected of having cancer cells. The candidate patient may also have been previously diagnosed as having cancer cells from diseases including, but not limited to, breast cancer, osteosarcoma, gastric cancer, non-small cell lung cancer, ovarian epithelial cancer and other cancers. Preferably, the candidate patient has breast cancer. In particularly preferred embodiments, the candidate patient has metastatic breast cancer cells.

In certain embodiments, the demonstration comprises comparing the copy number of HER-2/neu and one or more of the other markers to one or more suitable reference probes. For example, the copy number of chromosome 17 as measured by a peri-centromeric probe for chromosome 17 can be used as a reference for Her2 and/or TOP2A. In further embodiments, the method comprises step d) treating the candidate patient with trastuzumab.

The methods of the invention may comprise obtaining a tissue sample (e.g., a biopsy) comprising the cells from the candidate patient. In one embodiment the cells are breast cancer cells and the method further comprises contacting the tissue sample comprising the breast cancer cells with probes specific for HER-2/neu and TOP2A. The probes are sized so as not to overlap in their hybridization to the sample cells. In another embodiment, the cells are further contacted with a probe for a locus in the q arm of chromosome 1 (1q) extending approximately equidistant from the 1q25 locus to about the locus of the PTGS2 gene or an enumeration probe for chromosome 10. Such probes include probes for the specific loci 1q25 and PTGS2 and a pericentromeric probe for chromosome 10.

The present invention also provides kits and sets of probes for use in diagnosing and treating cancers, and preferably methods for determining the susceptibility of patients suspected of having cancer to successful treatment with medication that inhibits the signaling capability of the HER-2 receptor protein. Preferably, fluorescently labeled probes are used and included in the probe sets and kits of the invention. The kits and probe sets of the invention comprise probes able to detect copy numbers for both HER-2/neu and the q arm of chromosome 1 (1q), and chromosome 10. Probes for 1q may extend approximately equidistant from the 1q25 locus to about the locus of the PTGS2 gene. The kits and probe sets may further comprise probes for specific loci in the 1q region including the 1q25 locus and the PTGS2 gene. The kits and probe sets may also comprise a probe for TOP2A. The kits and probe sets may also comprise one or more suitable reference probes such as a probe able to enumerate chromosome 17. The kits of the invention may also include additional reagents for carrying out the methods of the invention.

DETAILED DESCRIPTION OF THE INVENTION

The invention includes methods for identifying candidate patients for treatment with medication that is believed to inhibit the signaling capability of the Her2 receptor protein, probe sets and kits for identifying the candidate patients, and the treatment of such patients. Preferably, the patients are breast cancer patients and the medication is trastuzumab.

Chromosomal Probes. Suitable probes for use in the in situ hybridization methods utilized with the invention fall into two broad groups: chromosome enumeration probes, i.e., probes that hybridize to a chromosomal region, usually a repeat sequence region, and indicate the presence or absence of an entire chromosome; and locus specific probes, i.e., probes that hybridize to a specific locus on a chromosome and detect the presence or absence of a specific locus. Chromosome arm probes, i.e., probes that hybridize to a chromosomal region and indicate the presence or absence of an arm of a specific chromosome, may also be useful. Chromosomal probes and combinations thereof are chosen for the ability to classify patients as to response to therapy when used in methods of the invention. Response to therapy is commonly classified as progressive disease (PD), stable disease (SD), partial response (PR), and complete response (CR). Good response is typically considered to include PR+CR (collectively referred to herein as Objective Response), but may also be expanded to include SD (referred to herein as Clinical Benefit), particularly when disease is severe. Probe sets can comprise any number of probes, e.g., 2, 3, 4 or more probes. The number of probes useful with the invention is limited only by the user's ability to detect the probes on an individual basis.

As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. Non-limiting examples of specific chromosome enumeration probes are the peri-centromeric probes for chromosomes 3, 10 and 17 described in the Examples.

A locus specific probe hybridizes to a specific, non-repetitive locus on a chromosome. Non-limiting examples of locus specific probes include probes to the gene loci Her2, 1q25, and TOP2A described in the Examples. Some loci comprise genes, e.g., oncogenes and tumor suppressor genes that are altered in some forms of breast cancer. Thus, probes that target these genes, including exons, introns, or regulatory chromosomal sequences of the genes, can be used in the identification methods described herein. Non-limiting examples of target genes include HER-2/neu, TOP2A, PTGS2 and AKT3.

Probes that hybridize with centromeric DNA and specific chromosomal loci are available commercially from Abbott Molecular Inc. (Des Plaines, Ill.) and Molecular Probes, Inc. (Eugene, Oreg.). Alternatively, probes can be made non-commercially using well known techniques. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Biotechnic Histochem, 1998, 73 (1): 6-22; Wheeless, et al., Cytometry, 1994, 17:319-327; and U.S. Pat. No. 5,491,224. Synthesized oligomeric DNA or PNA probes can also be used.

The size of the chromosomal region detected by the probes used in the invention can vary, for example, from the alpha satellite 171 base pair probe sequence noted above to a large segment of 900,000 bases. For locus-specific probes that are directly labeled, it is preferred to use probes of at least 100,000 bases in complexity, and to use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or protein nucleic acid as the blocking nucleic acid. For targeting a particular gene locus, it is preferred that the probes span approximately the entire genomic coding locus of the gene.

Chromosomal probes can contain any detection moiety that facilitates the detection of the probe when hybridized to a chromosome. Effective detection moieties include both direct and indirect labels as described below.

Chromosomal probes can be directly labeled with a detectable label. Examples of detectable labels include fluorophores (i.e., organic molecules that fluoresce after absorbing light), radioactive isotopes (e.g., $^{32}P$, and $^{3}H$) and chromophores (e.g., enzymatic markers that produce a visually detectable marker). Fluorophores are preferred and can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker.

The fluorophore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002 (hereafter cited as "Morrison 2002"), incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxycoumarin-3-carboxylic acid; 6-[fluorescein 5-(and-6)-carboxamido]hexanoic acid; N-(4,4-difluoro-5,7-dimethyl-4-bora-3a,4a diaza-3-indacenepropionic acid; eosin-5-isothiocyanate; erythrosine-5-isothiocyanate; 5-(and-6)-carboxyrhodamine 6G; and Cascade™ blue acetylazide (Molecular Probes, Inc., Eugene, Oreg.).

When multiple probes are used, fluorophores of different colors can be chosen such that each chromosomal probe in the set can be distinctly visualized. Preferably the probe panel of the invention will comprise two or three separate probes, each labeled with a separate fluorophore. Use of four probes may be preferred as providing the best balance between clinical sensitivity (sensitivity can increase with added probes) and imaging/detection complexity (complexity can increase with added probes). It is also within the scope of the invention to use multiple panels sequentially on the same sample: in this embodiment, after the first panel is hybridized, the results are imaged, the sample is destained and then is hybridized with a second panel. Multiple panels may also be hybridized each to a different portion of the same specimen, e.g. to serial sections from a paraffin block of a fixed and embedded specimen.

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard calorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase.

The probes and probe sets useful with the methods of the invention can be packaged with other reagents into kits to be used in carrying out the methods of the invention. Useful probe sets and kits can comprise probes to HER-2/neu and probes to one or more of the genetic loci 1q, 1q25 and the gene PTGS2 (1q31), and a probe to enumerate chromosome 10. Additionally, probe sets and kits may include a probe for TOP2A and/or one or more reference probes such as a probe to enumerate chromosome 17.

Pre-Selection of Cells. Cell samples can be evaluated preliminarily by a variety of methods and using a variety of criteria. The probes and methods described herein are not limited to usage with a particular screening methodology. One example is the "scanning method" wherein the observer scans hundreds to thousands of cells for cytologic abnormalities, e.g., as viewed with a DAPI filter. The number of cells assessed will depend on the cellularity of the specimen, which varies from patient to patient. Cytologic abnormalities commonly but not invariably associated with dysplastic and neoplastic cells include nuclear enlargement, nuclear irregularity, and abnormal DAPI staining (frequently mottled and lighter in color). In the scanning step, the observer preferably focuses the evaluation of the cells for chromosomal abnormalities (as demonstrated by FISH) to those cells that also exhibit cytological abnormalities. In addition, a proportion of the cells that do not have obvious cytologic abnormalities can be evaluated since chromosomal abnormalities also occur in the absence of cytologic abnormalities. This scanning method is described in further detail in U.S. Pat. No. 6,174,681 to Halling, et al., which is incorporated herein by reference. Breast cancer cells can be selected for evaluation using the method described in the PathVysion® FISH panel sold commercially by Abbott Molecular Inc. The product insert of the PathVysion FISH panel is incorporated herein by reference. This procedure uses an H&E stained slide from the same tumor block as the slide for FISH. The region of interest is selected by viewing the H&E stained slide, preferably by a pathologist, and the corresponding region is marked on the FISH slide. Cells with morphology consistent with malignancy (i.e. larger nuclei) are enumerated within the marked region of interest.

Preparation of Samples. The identification of a candidate patient (e.g., a breast cancer patient) for treatment with medication believed to inhibit the signaling capability of the HER-2 receptor protein or otherwise comparable to trastuzumab can be determined by identifying chromosomal aberrations in an appropriate biological sample obtained from the patient. This can be accomplished by in situ hybridization. In general, in situ hybridization includes the steps of fixing a biological sample, hybridizing a chromosomal probe to target DNA contained within the fixed sample, washing to remove non-specifically bound probe, and detecting the hybridized probe. The in situ hybridization can also be carried out with the specimen cells in liquid suspension, followed by detection by flow cytometry. Alternatively, gene copy number and amplification can be assessed by other methods, including the polymerase chain reaction (PCR). Descriptions of measuring the HER2 gene by PCR are contained within the following articles as examples: Willmore, et al., (2005) Applied Immunohistochemistry and Molecular Morphology 13(4):333-341; Lyon et al. (2001) Clinical Chemistry 47(5): 844-851; Li et al. (1994) 73(11):2771-2778, and O'Malley et al. (2001) American Journal of Clinical Pathology 115(4): 504-511.

Abnormal cells are characterized by abnormal numbers of chromosomes within the cells and/or structural alterations within the cells' chromosomes. Structural alterations can include gains or losses (e.g., hemizygous or homozygous loss) of a specific chromosomal region, such as a locus or centromeric region as indicated in the Examples. Positive test indicators can be developed accordingly. For example, a cell having one or more chromosomal gains, i.e., three or more copies of any given target locus, can be considered to test positive in the methods described herein. Cells exhibiting monosomy or nullisomy may also be considered test positive under certain circumstances.

A biological sample is a sample that contains cells or cellular material, e.g., cells or material derived from the breast. Examples of breast specimens include breast biopsies and the like. Typically, cells are harvested from a biological sample and prepared using techniques well known in the art. Numerous methods are available for collecting cells for evaluation. For example, cells from the breast are collected using well-known techniques such as fine needle aspiration (FNA). Conventional cytological smears are prepared by spreading cells evenly and thinly onto a glass slide. The slide is then fixed rapidly by immersion into 95% ethanol or spraying with a commercial fixative according to manufacturer instructions. Breast cells are also collected for histology by core biopsy or surgical biopsy, and are typically fixed in formalin solution and embedded in paraffin.

Detection of Chromosomal Abnormalities. Gain or loss of chromosomes or chromosomal regions within a cell is assessed by examining the hybridization pattern of the chromosomal probe or set of chromosomal probes (e.g., the number of signals for each probe) in the cell, and recording the number of signals. Test samples can comprise any number of cells that is sufficient for a clinical diagnosis, and typically contain at least about 100 cells. In a typical assay, the hybridization pattern is assessed in about 20-200 cells. Test samples are typically considered "test positive" for abnormality of a particular genetic locus when found to contain a plurality of cells containing the abnormality (e.g., gain or loss of the locus). Criteria for "test positive" can include testing positive with one, two, three, four or more probes depending upon the clinical correlation between the abnormal loci and patient response to therapy. In addition, when multiple probes are used test positive can include detection of abnormal hybridization patterns with a subset of probes. For example, a combination of gains or losses of a subset of the probes, e.g., two or three probes of a full set of four probes, can result in a positive test result. Hybridization patterns can also be assessed in sequence for subsets of probes. For example, the pattern of an initial subset of probes (e.g., the probes to the HER-2 and TOP2A loci) can be assessed and, if a positive result is indicated from the subset of probes the test can be taken as positive overall.

However, if the initial result is not positive, the pattern for an additional subset of probes (e.g., a probe to the 1q25 locus) can be assessed to complete the test. If the combined result for all probes indicates a positive test result, the test can be taken as positive overall.

The number of cells identified with chromosomal abnormalities and used to classify a particular sample as positive, in general will vary with the number of cells in the sample. The absolute number of cells detected with chromosomal abnormality or the percentage of the total number of cells examined that contain the abnormality, can be used to determine if a sample is positive by comparison to a cutoff value. If, for example, the number or percentage of cells with abnormality is equal to or below the cutoff value then the specimen can be classified as negative for the abnormality. If the number or percentage of cells with abnormality is greater than the cutoff value then the specimen can be classified as positive. Specimens positive for one or a particular set of chromosomal abnormalities can be classified as to the patient's probable response to medication. Alternatively, specimen positivity with respect to a chromosomal abnormality can be determined from the average copy number of a locus per cell in the specimen or the average ratio of one locus copy number to a second locus copy number for that specimen. Specimens having average copy numbers of a particular locus per cell above a cutoff established for abnormal gain of a locus, or below a cutoff established for abnormal loss of a locus are considered positive for the specific abnormality. Likewise cutoffs can be established for the relative gain or loss between two different loci and applied to the measured loci ratio to establish if a sample is positive or negative for that abnormality.

Details of the invention are further described in the following examples, which are not intended to limit the scope of the invention as claimed. One of skill in the art will recognize that variations and modifications of the invention may be apparent upon reviewing the instant specification. It is therefore an object to provide for such modifications and variations of the embodiments described herein, without departing from the scope or the spirit of the invention.

EXAMPLES

Hybridization Probes. The following clones were used as FISH mapping probes: 291U (from a BAC or PAC library of the Roswell Park Cancer Institute (RPCI), designated RPCI-11-283123), 291P (RPCI-5-1152A16), 291F (from a BAC library of the California Institute of Technology (CIT), designated CITC-428H21), LSI® TOP2A (291Z.2; Abbott Molecular Inc.), 291Z.7 (RPCI-11-89A22), and 291Z.8 (RPC-11-1028K7). The mapping clones lie within a contiguous region beginning about 114 kb telomeric of the Vysis LSI HER-2 probe and extending for approximately 650 kb toward the 17q telomere. Each in situ hybridization with the mapping probes included 3 FISH probes directly labeled with different fluorophores: a peri-centromeric probe for chromosome 17 (SpectrumAqua™ CEP® 17; Abbott Molecular Inc.), SpectrumGreen™ LSI HER-2 (Abbott Molecular Inc.) and one of the 6 mapping probes labeled with SpectrumOrange™.

The following clones were used as signal transduction probes: LSI PTEN (Abbott Molecular Inc.), LSI 1q25 (Abbott Molecular Inc.), PTGS2 (RPCI-11-70N10, RPCI-11-809F11, RPCI-11-104B23, RPCI-11-457L10, RPCI-11-33912), PIK3CA (RPCI-11-355N16, CITD-2354L18, CITD-3030M16, RPCI-11-360P21, CITD-2109M3, CITD-2537A7), and AKT3 (CITD-2011E13, RPCI-11-351N5, RPCI-11-119H6). Signal transduction probes were hybridized in 3- and 4-color probe panels with each probe directly labeled with a spectrally distinct fluorophore. Panel 1 included: SpectrumGreen LSI 1q25, SpectrumGold™ PTGS2, SpectrumRed™ AKT3. Panel 2 included: A peri-centromeric probe for chromosome 3 (SpectrumGreen CEP 3; Abbott Molecular Inc.), SpectrumGold Pik3CA, SpectrumRed PTEN and a peri-centromeric probe for chromosome 10 (SpectrumAqua CEP 10; Abbott Molecular Inc.). Probes not commercially available were labeled according to the methods disclosed in U.S. Pats. Nos. 5,491,224 and 5,506,350 incorporated herein by reference. Probes were dissolved in hybridization solution comprised of 7 parts Vysis LSI Hybridization Buffer and 3 parts water. Probes and reagents designated with LSI, CEP, or Vysis in the name are commercial products obtained from Abbott Molecular, Inc., Des Plaines, Ill.

Specimens. Seventy patients with metastatic breast carcinoma who had been treated at Rush Presbyterian St. Luke's Medical Center, Chicago, Ill. with trastuzumab between 1997 and 2004 were considered for the study. This comprised all trastuzumab-treated metastatic breast cancer patients for whom adequate archival pretherapy tumor tissue was available in the Pathology archives. The study was approved by the Rush Institutional Review Board. The patients had been treated either with trastuzumab alone or in combination with conventional chemotherapy, a taxane in almost all cases. Essentially all of the patients had been extensively treated previously with a variety of chemotherapy regimens. After an intensive chart review of these patients, it was determined 35 of them had either progressed while on trastuzumab (PD), had stable disease (SD) for at least six months, a partial response (PR), or a complete response (CR), according to RECIST criteria. These 35 patients were deemed suitable for inclusion in the study. For the other patients, the available medical records either did not clearly indicate whether or not the patient responded to trastuzumab, or informative medical records were unavailable.

The diagnosis of breast carcinoma in the archival material was confirmed by histologic evaluation before further analysis. There was sufficient archival material available for all of the patients included to ensure that the study did not exhaust the diagnostic tumor tissue.

Paraffin blocks containing tissue biopsy specimens were sectioned at 5 μm thickness and mounted onto SuperFrost Plus® positively charged slides (ThermoShandon, Pittsburgh, Pa.). All slides were baked at 56° C. overnight to fix the tissue onto the slides, and were then stored at room temperature.

In Situ Hybridization: In preparation for in situ hybridization, specimen slides were de-paraffinized by soaking in 3 changes of Hemo-De™ Solvent and Clearing Agent (Scientific Safety Solvents, Keller, Tex.) for 5 minutes each, followed by two 1-minute rinses in absolute ethanol. After drying, the specimens were further prepared for in situ hybridization by immersion of the slides in Vysis Pretreatment Solution (sodium thiocyanate-based chaotrope solution) at 80° C. for 10 minutes, and rinsing in water for 5 minutes. The slides were then immersed in a solution of 4 mg pepsin (2500-3000 U/mg) per ml 0.2 N HCl at 37° C. for 15 minutes, rinsed in water for 3 minutes, dehydrated in 70%, 85%, and 100% ethanol for 1 minute each, and allowed to dry. Pretreatment solution, 0.2N HCL, and pepsin are available commercially in kit form (Paraffin Pretreatment 2, cat #32-191095, Abbott Molecular, Inc.).

The prepared specimen slides were hybridized with FISH probe solutions in a HYBrite™ automated co-denaturation oven (Abbott Molecular, Inc.). The slides were placed on the oven surface, probe solution was placed over the tissue section (typically 10 μl), a coverslip was applied over the probe solution, and the edges of the coverslip were sealed to the slide with rubber cement. The oven co-denaturation/hybridization cycle was set for denaturation at 73° C. for 5 minutes, and hybridization at 37° C. for 16-18 h. After hybridization, the slides were removed from the HYBrite, and the rubber cement was removed. The slides were placed in room-temperature 2×SSC(SSC=0.3 M NaCl, 15 mM sodium citrate)/0.3% Nonidet P40 (NP40; Abbott Molecular, Inc.) for 2 to 10 minutes to remove the coverslips. The slides were then immersed in 73° C. 2×SSC/0.3% NP40 for 2 minutes for removal of nonspecifically bound probe, and allowed to dry in the dark. DAPI I antifade solution (1000 ng DAPI/ml in antifade mounting solution; Abbott Molecular, Inc.) was applied to the specimen to allow visualization of the nuclei.

Some of the specimens required additional processing to yield optimal FISH results. Overdigested specimens were re-processed starting with a new specimen slide. These slides were processed under milder conditions (Vysis Paraffin Pretreatment I protocol and reagents, as described previously (Jacobson et al., 2000)). Those slides that were underdigested were exposed to additional treatment as follows. First, the coverslips were removed by soaking the slides in 2×SSC/0.3% NP40 at room temperature. Next, the slides were rinsed in purified water and were incubated for 5-10 minutes in 4 mg pepsin/0.2 N hydrochloric acid at 37° C. The slides were rinsed in purified water again, and were passed through an ethanol dehydration series. After drying, the slides were re-hybridized under the same conditions as used for the original hybridization.

Enumeration of FISH Signals. The FISH slides were evaluated under a Zeiss Axioscope epi-fluorescence microscope (Carl Zeiss, Thornwood, N.Y.). Signals were visualized and counting was performed using DAPI single-band-pass filter sets to visualize nuclei (an orange single-band-pass filter set to visualize SpectrumOrange-labeled probes, a green single-band-pass filter set to visualize SpectrumGreen probes, an aqua single-band-pass filter set to visualize SpectrumAqua probes, a red single-band-pass filter set to visualize SpectrumRed probes, and a gold single-band-pass filter set to visualize SpectrumGold probes (all filter sets from Abbott Molecular Inc.)). A minimum of 30 nuclei with malignant morphology were counted. For each probe and each specimen, the mean number of signals per cell was calculated by totaling the number of corresponding probe signals across all cells enumerated and dividing by the total number of enumerated cells. Mean HER-2 and mapping probe signals per cell were divided by the mean CEP 17 signals per cell to yield the average number of each target per chromosome 17. Ratios between other loci were calculated in the same manner by dividing the mean signals per cell for one locus by the mean signals per cell of the other locus. When a slide was counted multiple times, the mean probe signals per cell from each evaluation were averaged together and used for recalculating the ratios.

For HER-2 a ratio of 2.0 HER-2/CEP 17 or greater was considered to be amplification because this value has been used in a number of published studies investigating HER-2 amplification and its relationship to expression and patient outcome (Pauletti et al., 1996, 2000; Pauletti and Slamon, 1999; Persons et al., 2000). Since TOP2A and the targets of the other mapping probes are associated with the HER-2 amplicon when amplified, the same cutoff of 2.0 was used to distinguish amplified from nonamplified specimens in initial evaluations. The cutoff used for deletion was 0.75 (Jacobson et al. 2004). Each of the other loci was evaluated using signals per cell as well as ratios when applicable. Multiple sets of cutoff values were selected for categorizing each target locus. Final cutoff values were selected based on the ability to discriminate between good and poor patient response to therapy. CR or PR was categorized as objective response, and PD or SD was categorized as poor response or lacking response. Clinical benefit was defined as CR, PR, or SD.

In order to conserve valuable specimens from trastuzumab-treated patients, a strategy for hybridizing the mapping probes was developed that minimized the number of required hybridizations. The published mapping study (Jacobson et al., 2004) demonstrated a predominantly contiguous pattern of amplification within the 17q mapping region in which Her-2 resides. That is, if one of the mapping probes lying telomeric to HER-2 was amplified, then all probes lying between that probe and HER-2 also showed amplification. This was true in 67 of the 75 tumors evaluated (89%). Therefore, to minimize the number of specimen sections utilized, mapping probes were hybridized beginning with the LSI® TOP2A probe. If the status of the specimen was found to be amplified for TOP2A (cutoff value of 2.0) all mapping clones centromeric to TOP2A were not tested and were assumed to be amplified). The probe 291Z.7 was then tested, and if amplified, the contiguous clone centromeric to 291Z.7, 291Z.8, was not tested and was assumed to be amplified. If 291Z.7 was not amplified, then 291Z.8 was tested. However, if specimens were not amplified for LSI® TOP2A, then 291P was tested. If 291P was amplified, then 291F was tested and if 291P was not amplified then 291U was tested, indicating the telomeric-most amplified target and establishing the telomeric limit of the HER-2 amplicon.

Signal transduction probes were analyzed using average probe signals per cell or ratios of probe signals per reference chromosome to classify specimens as normal, gained, deleted, or amplified for particular loci. Effective classification of patients relative to response was achieved using cutoffs of 3.0 and 1.5 signals/cell for gain and loss of the 1q25 locus, respectively, 2.75 and 1.6 signals/cell for gain and loss of the PTGS2 locus, respectively, and 2.75 and 1.7 signals/cell for gain and loss of chromosome 10 (CEP 10), respectively. Cutoffs of 3.0 and 1.6 signals/cell for gain and loss of the AKT3 locus, respectively, provided optimal classification, though not statistically significant.

For ratios of HER-2 or mapping probes to chromosome 17 (represented by CEP 17 signals), ratios of 2.0 or greater were classified as amplified, ratios between 0.75 and 2.0 were classified as normal, and ratios less than or equal to 0.75 were classified as deleted (Jacobson et al., 2004). For the signal transduction probes, cutoffs were established empirically in order to maximize the correlation between patient response and the genetic statuses of the loci. Cutoff values less than 2 signals/cell were examined to delineate deletion of a locus from normal copy number, and cutoff values greater than 2 were examined to delineate gain of a locus from normal copy number. Contingency analysis was used to categorize patient response relative to genomic status, and p-values were calculated using Fisher's exact test (2-sided; <0.05 considered significant).

Results

Enumeration Results. Of the 70 patients considered for the study, 35 had both interpretable responses to therapy and specimens that yielded enumerable FISH signals for the mapping probes. Thirty-four specimens yielded enumerable FISH signals for the signal transduction pathway probes. One specimen of the 35 patients contained two unique tumor clones; the more abnormal of the clones was selected to be analyzed. All 35 tumors contained sufficient material to allow completion of the mapping and signal transduction probe sets study.

Overeall Response to Therapy. Response to therapy was considered both as Objective Response (CR+PR) and as Clinical Benefit (SD+CR+PR). Objective Response was found in 14 (40%) of the 35 patients, compared to 20 (57%) of the 35 patients showing Clinical Benefit (Table 1).

TABLE 1

Summary of Response to Therapy

| Response to Therapy | | | | | |
|---|---|---|---|---|---|
| CR | PR | SD | PD | Objective Response (%) | Clinical Benefit (%) |
| 10 | 4 | 6 | 15 | 14/35 (40%) | 20/35 (57%) |

CR means complete response;
PR means partial response;
SD means stable disease; and
PD means progressive disease.

HER-2/TOP2A Mapping. For patients with amplicons not extending beyond the HER-2 probe region, 57% had objective response. For amplicons extending to each of the 6 mapping probes telomeric from HER-2, objective responses were found in 50%, 100%, 67%, 0%, 0%, and 12.5% respectively (Table 2). Fifty seven percent of patients with amplicons not extending beyond HER-2 showed Clinical Benefit For amplicons extending to each of the 6 mapping probes telomeric from HER-2, Clinical Benefit was found in 67%, 100%, 100%, 25%, 50%, and 50% respectively. These data indicate that response is best when the amplicon does not contain the TOP2A locus. Grouping patients into those whose amplicon does not extend to the TOP2A locus and those whose amplicon includes the TOP2A locus, Objective Response was found in 62% (13/21) in the former group and 7.1% (1/14) in the lattergroup (p=0.0015). Clinical Benefit was found in 67% (14/21) in the former group and 43% (6/14) in the latter group (p=0.19). These data show that the gene status of TOP2A is a strong predictor of Objective Response, identifying a group of patients (HER-2 amplified and non-amplified TOP2A) that responds over 1.5-fold better than the overall (unselected) response rate, and identifying a second group (HER-2 and TOP2A amplified) that will receive little benefit from trastuzumab therapy. In terms of Clinical Benefit, the improvement in patient classification provided by TOP2A status is marginal. Generally speaking, Objective Response is considered more informative than Clinical Benefit since it can be difficult to know if SD is the result of the treatment.

The two mapping loci on either side of the TOP2A locus, 291F and 291Z.8, also provided classification of patients as to Objective Response to trastuzumab that was an improvement over HER-2 amplification alone. For the 291F locus, Objective Response was found in 60% (9/15) of the HER-2 amplified and 291F non-amplified group and 25% (5/20) when 291F was amplified (p=0.080, marginal statistical significance). For the 291Z.8 locus, Objective Response was found in 52% (13/25) of the HER-2 amplified and 291F non-amplified group and 10% (1/10) when 291F was amplified (p=0.028).

TABLE 2

Summary of Response to Therapy For Mapping Probes Tested

| Response to Therapy | HER-2 | 291U | 291P | 291F | TOP2A | 291Z.8 | 291Z.7 |
|---|---|---|---|---|---|---|---|
| Objective Response (%) | 4/7 (57%) | 3/6 (50%) | 2/2 (100%) | 4/6 (67%) | 0/4 (0%) | 0/2 (0%) | 1/8 (12.5%) |
| Clinical Benefit (%) | 4/7 (57%) | 4/6 (67%) | 2/2 (100%) | 4/6 (67%) | 1/4 (25%) | 1/2 (50%) | 4/8 (50%) |

Growth Factor Signaling Pathways. Specific loci for components of the ERBB growth factor signaling pathway were assessed by FISH for correlation with response to trastuzumab in breast cancer patients. Data were analyzed as ratios as well as signals per cell with cutoff values being determined based upon response to therapy. Data presented here are based upon signals per cell. Three regions of interest were studied on chromosome 1 including 1q25, the PTGS2 locus (1q31) and the AKT3 locus (1q43). Of the 34 samples tested, 59-74% of specimens were abnormal (gained or deleted loci). 1q25 and PTGS2 gains and deletions were associated with good response to therapy (Table 3). For 1q25, 75% (15/20) of abnormal specimens showed Clinical Benefit from therapy compared to only 29% (4/14) of normal specimens (p=0.0135). PTGS2 had 64% (16/25) of abnormal specimens and 33% (3/9) of normal specimens associated with Clinical Benefit (p=0.139), and AKT3 had 62% (13/21) of abnormal specimens and 46% (6/13) of normal specimens associated with Clinical Benefit (p=0.484). Association with Clinical Benefit for PTGS2 and AKT3 was not statistically significant. Considering objective response, 1q25 showed 60% (12/20) response in abnormal patients and 14% (2/14) response in normal patients (p=0.0128). PTGS2 showed 52% (13/25) Objective Response in abnormal patients and 11% (1/9) response in normal patients (p=0.051). These values were significant for 1q25 and of borderline statistical significant for PTGS2. AKT3 gain and loss were not correlated with response to therapy although a similar trend as is seen with 1q25 and PTGS2 is seen in that a larger number of abnormal specimens compared with normal specimens are responsive to therapy (Table 3).

Probes for the signaling pathway genes PIK3CA and PTEN and the respective centromeric probes for chromosomes 3 and 10 were analyzed for correlation with response to trastuzumab in breast cancer patients. Chromosome 3, PIK3CA and PTEN had no significant correlation with response to therapy, either Objective Response or clinical benefit. Chromosome 10 gains and losses, however, correlated with good response to trastuzumab (Table 4). Objective Response was found in 75% (9/12) of patients with abnormal Chromosome 10, and in 23% (5/22) of patients with normal Chromosome 10 (p=0.0048). Clinical Benefit was found in 83% (10/12) of patients with abnormal Chromosome 10 and 41% (9/22) of patients with normal Chromosome 10 (p=0.030).

Contingency analysis was also used to categorize response relative to the combined genomic statuses of two loci. When TOP2A amplification, 1q25, PTGS2, or Chromosome 10 abnormalities were combined in pairs, targeting of samples could be improved over the use of a single locus. When Chromosome 10 was combined with 1q25, PTPGS2 or TOP2A by contingency analysis sensitivity for detection of responders and nonresponders increased. Contingency analyses combining data from Chromosome 10 and the 1q25 locus identified a pure population of responders to therapy. Patients that were abnormal for both Chromosome 10 and 1q25 showed 100% (8/8) Clinical Benefit from therapy while 42% (11/26) of other patients showed benefit (p=0.0045). Objective Response was found in 88% (7/8) of patients with both abnormal Chromosome 10 and 1q25 while 27% (7/26) of other patients showed response (p=0.0039).

Patients with nonamplified TOP2A combined with abnormal 1q25 showed Clinical Benefit in 86% (12/14) of patients compared to 35% (7/20) showing benefit in other patients (p=0.0051). Patients with nonamplified TOP2A combined with abnormal 1q25 showed Objective Response in 79% (11/14) of patients compared to 15% (3/20) showing benefit in other patients (p=0.0003).

Analysis of Chromosome 10 and the PTGS2 loci identified a pure population of nonresponders to therapy. Patients normal for both loci had 0% (0/8) Objective Response while 64% (14/26) of other patients had response (p=0.0109). Comparison based on Clinical Benefit did not provide a significant correlation.

Patients with nonamplified TOP2A combined with abnormal PTGS2 showed Clinical Benefit in 76% (13/17) of patients compared to 35% (6/17) showing benefit in other patients (p=0.037). Patients with nonamplified TOP2A combined with abnormal PTGS2 showed Objective Response in 71% (12/17) of patients compared to 15% (3/20) showing benefit in other patients (p=0.0013).

TABLE 3

Summary of FISH Results on Patients Showing Response to Therapy

| Loci | | Abnormal | | | | Loci | | Abnormal | | | |
| --- | --- | --- | --- | --- | --- | --- | --- | --- | --- | --- | --- |
| | | Gain | Loss | Normal | P* | | | Gain | Loss | Normal | P* |
| 1q25 | Clinical Benefit | 15 | | 4 | 0.0135 | 1q25 | Objective Response | 12 | | 2 | 0.0128 |
| | $CO_{gain} = 3.0$ | 13 | 2 | | | | $CO_{gain} = 3.0$ | 10 | 2 | | |
| | $CO_{loss} = 1.5$ | | | | | | $CO_{loss} = 1.5$ | | | | |
| PTGS2 | Clinical Benefit | 16 | | 3 | 0.1392 | PTGS2 | Objective Response | 13 | | 1 | 0.0504 |
| | $CO_{gain} = 2.75$ | 13 | 2 | | | | $CO_{gain} = 2.75$ | 11 | 2 | | |
| | $CO_{loss} = 1.6$ | | | | | | $CO_{loss} = 1.6$ | | | | |
| AKT3 | Clinical Benefit | 13 | | 6 | 0.48 | AKT3 | Objective Response | 10 | | 4 | 0.48 |
| | $CO_{gain} = 3.0$ | 11 | 2 | | | | $CO_{gain} = 3.0$ | 8 | 2 | | |
| | $CO_{loss} = 1.6$ | | | | | | $CO_{loss} = 1.6$ | | | | |

*Fisher's exact test (2-sided; <0.05 considered significant) comparing response to therapy between normal and abnormal patients.

TABLE 4

Summary of Response to Therapy: CEP 10

| CEP 10 | Abnormal | | Normal | P* | CEP 10 | Abnormal | | Normal | P* |
| --- | --- | --- | --- | --- | --- | --- | --- | --- | --- |
| | Gain | Loss | | | | Gain | Loss | | |
| Clinical Benefit | 10 | | 9 | 0.0297 | Objective Response | 9 | | 5 | 0.0048 |
| $CO_{gain} = 2.75$ | 2 | 8 | | | $CO_{gain} = 2.75$ | 2 | 7 | | |
| $CO_{loss} = 1.7$ | | | | | $CO_{loss} = 1.7$ | | | | |

Identification of Breast Cancer Patients for Treatment with Trastuzumab (Herceptin®). LSI TOP2A/HER-2/CEP 17: The 3-color color probe set LSI TOP2A/HER-2/CEP 17 Multi-Color Probe commercially available from Vysis, Inc. can be used for stratifying breast cancer patients for treatment with trastuzumab. Breast biopsy samples can be prepared for FISH hybridization and subject to hybridization with the probe set as described above. Cells from each sample can be evaluated by enumerating 20 to 200 sequential cells, as described above. Samples amplified for HER-2 and demonstrating signal ratios of the TOP2A-to-centromere 17 loci that are less than a cutoff of 2.0 can be considered positive for treatment with trastuzumab, while other patients can be considered less suitable candidates for treatment with trastuzumab. Examples for two patients (Patients 1 and 2) are as follows.

Patients 1 and 2

Formalin-fixed, paraffin embedded breast tumor tissue from Patients 1 and 2 were processed for FISH, and FISH performed, as described above, using the Vysis LSI TOP2A SpectrumOrange/LSI HER2 SpectrumGreen/CEP 17 SpectrumAqua multi-color probe set (Abbott Molecular, Inc.). The slides were evaluated on a fluorescence microscope as described above and the number of signals corresponding to the TOP2A, HER2, and CEP 17 probes was determined for 30 cells. The results are collected in Tables 5A and 5B.

TABLE 5

Signal Counts for Patients 1 and 2.

| Table 5A. Patient 1 | | | | Table 5B. Patient 2 | | | |
| --- | --- | --- | --- | --- | --- | --- | --- |
| Cell No. | TOP2A | HER2 | CEP 17 | Cell No. | TOP2A | HER2 | CEP 17 |
| 1 | 1 | 8 | 1 | 1 | 7 | 14 | 2 |
| 2 | 1 | 11 | 1 | 2 | 7 | 10 | 1 |
| 3 | 2 | 14 | 2 | 3 | 3 | 8 | 1 |
| 4 | 1 | 11 | 1 | 4 | 7 | 8 | 1 |
| 5 | 1 | 18 | 1 | 5 | 7 | 8 | 2 |
| 6 | 1 | 11 | 1 | 6 | 5 | 5 | 2 |
| 7 | 1 | 8 | 1 | 7 | 6 | 10 | 2 |
| 8 | 1 | 11 | 1 | 8 | 4 | 7 | 2 |
| 9 | 1 | 10 | 1 | 9 | 6 | 10 | 2 |
| 10 | 1 | 16 | 1 | 10 | 7 | 9 | 2 |
| 11 | 1 | 12 | 2 | 11 | 6 | 7 | 1 |
| 12 | 1 | 11 | 1 | 12 | 6 | 6 | 2 |
| 13 | 1 | 10 | 2 | 13 | 7 | 10 | 2 |
| 14 | 1 | 11 | 1 | 14 | 6 | 7 | 1 |
| 15 | 1 | 10 | 1 | 15 | 7 | 10 | 1 |
| 16 | 1 | 11 | 2 | 16 | 7 | 6 | 2 |
| 17 | 1 | 8 | 1 | 17 | 10 | 7 | 2 |
| 18 | 1 | 15 | 1 | 18 | 7 | 9 | 1 |
| 19 | 1 | 11 | 1 | 19 | 6 | 10 | 1 |
| 20 | 1 | 10 | 1 | 20 | 5 | 7 | 1 |
| 21 | 1 | 12 | 1 | 21 | 7 | 8 | 2 |
| 22 | 1 | 10 | 1 | 22 | 5 | 9 | 1 |
| 23 | 1 | 12 | 1 | 23 | 6 | 9 | 2 |
| 24 | 1 | 14 | 1 | 24 | 7 | 7 | 2 |
| 25 | 2 | 13 | 1 | 25 | 7 | 10 | 2 |
| 26 | 1 | 12 | 1 | 26 | 7 | 11 | 2 |
| 27 | 1 | 12 | 1 | 27 | 6 | 11 | 2 |
| 28 | 1 | 9 | 1 | 28 | 6 | 9 | 2 |
| 29 | 1 | 11 | 2 | 29 | 4 | 10 | 2 |
| 30 | 1 | 2 | 1 | 30 | 5 | 10 | 2 |

Results for Patient 1: From these signal counts the average TOP2A/cell, HER2/cell and CEP 17/cell were calculated to be 1.07, 11.1, and 1.17, respectively, providing a value of 0.91 TOP2A/CEP 17 and 9.5 HER2/CEP 17 for this specimen. Since HER2 is amplified (HER2/CEP 17≦2.0) and TOP2A is not amplified (TOP2A/CEP 17<2.0), the patient is considered a very good candidate good for trastuzumab therapy. Patient 1 was treated with trastuzumab and showed a complete response to the drug by RECIST criteria.

Results for Patient 2: From these signal counts the average TOP2A/cell, HER2/cell and CEP 17/cell were calculated to be 6.20, 8.73, and 1.67, respectively, providing a value of 3.7 TOP2A/CEP 17 and 5.2 HER2/CEP 17 for this specimen. Since HER2 is amplified (HER2/CEP 17≧2.0) the patient is a potential candidate for trastuzumab therapy, however, since TOP2A is amplified also (TOP2A/CEP 17≧2.0), the patient is less likely to respond to treatment than patients for which TOP2A is not amplified, and alternative treatments should be considered. Patient 2 was treated with trastuzumab and showed progressive disease by RECIST criteria.

LSI Her-2, LSI TOP2A, CEP 17 and LSI 1q25: The 4 probes LSI Her-2, LSI TOP2A, CEP 17 and LSI 1q25 can be used for stratifying breast cancer patients for treatment with trastuzumab. The Vysis SpectrumOrange LSI TOP2A/SpectrumGreen LSI HER2/SpectrumAqua CEP 17 multi-color probe set can be used as a source for these probes. The SpectrumGreen LSI 1q25 probe described above can be hybridized in a second hybridization, or labels can be changed to allow hybridization and analysis of all 4 probes simultaneously (e.g. using SpectrumAqua, SpectrumGreen, SpectrumGold, and SpectrumRed labels). Breast biopsy samples were prepared for FISH hybridization and subject to hybridization as described above. Cells from each sample were evaluated by enumerating 20 to 200 sequential cells, as described above. Samples amplified for HER-2 and demonstrating signal ratios of the TOP2A-to-centromere 17 loci that are less than a cutoff of 2.0, and demonstrating 1q25 signals per cell that are either greater than a cutoff of 3.0 or less than a cutoff of 1.5 are considered positive for treatment with trastuzumab, while other patients are considered less suitable candidates for treatment with trastuzumab. Examples for two patients (Patients 3 and 4) are as follows.

Patients 3 and 4.

Formalin-fixed, paraffin embedded breast tumor tissue from Patients 3 and 4 were processed for FISH, and FISH performed, as described above, using the Vysis LSI TOP2A SpectrumOrange/LSI HER2 SpectrumGreen/CEP 17 SpectrumAqua multi-color probe set (Abbott Molecular, Inc.) on one set of slides and the Vysis SpectrumGreen LSI 1q25/SpectrumGold PTGS2/SpectrumRed AKT3 probe set as a source of 1q25 probe on a separate set of slides. The slides were evaluated on a fluorescence microscope as described above and the number of signals corresponding to the TOP2A, HER2, CEP 17 and 1q25 probes was determined for 30 cells. The results are collected in Tables 6 and 7.

TABLE 6

Signal Counts for Patient 3.

| Cell No. | TOP2A | HER2 | CEP 17 | Cell No. | 1q25 |
| --- | --- | --- | --- | --- | --- |
| 1 | 4 | 23 | 5 | 1 | 2 |
| 2 | 4 | 13 | 6 | 2 | 3 |
| 3 | 4 | 13 | 6 | 3 | 1 |
| 4 | 4 | 13 | 4 | 4 | 1 |
| 5 | 3 | 18 | 3 | 5 | 3 |
| 6 | 2 | 18 | 2 | 6 | 3 |
| 7 | 6 | 18 | 6 | 7 | 3 |
| 8 | 5 | 18 | 7 | 8 | 3 |
| 9 | 3 | 18 | 5 | 9 | 4 |
| 10 | 3 | 28 | 7 | 10 | 6 |
| 11 | 2 | 18 | 5 | 11 | 9 |
| 12 | 4 | 18 | 7 | 12 | 6 |
| 13 | 5 | 18 | 6 | 13 | 2 |
| 14 | 3 | 13 | 2 | 14 | 5 |
| 15 | 5 | 18 | 6 | 15 | 6 |
| 16 | 4 | 18 | 5 | 16 | 6 |
| 17 | 4 | 18 | 2 | 17 | 5 |
| 18 | 4 | 23 | 3 | 18 | 5 |
| 19 | 2 | 23 | 4 | 19 | 3 |
| 20 | 4 | 13 | 3 | 20 | 1 |
| 21 | 3 | 13 | 4 | 21 | 2 |
| 22 | 2 | 13 | 2 | 22 | 6 |
| 23 | 2 | 18 | 2 | 23 | 6 |
| 24 | 2 | 23 | 2 | 24 | 3 |
| 25 | 3 | 13 | 4 | 25 | 4 |
| 26 | 2 | 13 | 2 | 26 | 4 |
| 27 | 2 | 13 | 3 | 27 | 3 |
| 28 | 1 | 13 | 2 | 28 | 8 |
| 29 | 3 | 8 | 1 | 29 | 6 |
| 30 | 2 | 13 | 2 | 30 | 5 |

Results for Patient 3: From these signal counts the average TOP2A/cell, HER2/cell, CEP 17/cell, and 1q25/cell were calculated to be 3.2, 16.2, 3.9, and 4.1, respectively, providing a value of 0.82 TOP2A/CEP 17 and 4.1 HER2/CEP 17 for this specimen. Since HER2 is amplified (HER2/CEP 17≧2.0) and TOP2A is not amplified (TOP2A/CEP 17<2.0), and 1q25 is abnormal (1q25/cell≧3.0 or <1.5) the patient is considered a very good candidate good for trastuzumab therapy. Patient 3 was treated with trastuzumab and showed a complete response to the drug by RECIST criteria.

TABLE 7

Signal Counts for Patient 4.

| Cell No. | TOP2A | HER2 | CEP 17 | Cell No. | 1q25 |
| --- | --- | --- | --- | --- | --- |
| 1 | 10 | 17 | 1 | 1 | 3 |
| 2 | 5 | 7 | 1 | 2 | 3 |
| 3 | 7 | 8 | 1 | 3 | 2 |
| 4 | 11 | 14 | 2 | 4 | 3 |

TABLE 7-continued

Signal Counts for Patient 4.

| Cell No. | TOP2A | HER2 | CEP 17 | Cell No. | 1q25 |
| --- | --- | --- | --- | --- | --- |
| 5 | 14 | 13 | 3 | 5 | 3 |
| 6 | 9 | 11 | 2 | 6 | 1 |
| 7 | 12 | 14 | 2 | 7 | 1 |
| 8 | 11 | 14 | 2 | 8 | 2 |
| 9 | 12 | 14 | 2 | 9 | 3 |
| 10 | 12 | 12 | 2 | 10 | 2 |
| 11 | 13 | 15 | 2 | 11 | 2 |
| 12 | 12 | 14 | 1 | 12 | 3 |
| 13 | 11 | 12 | 2 | 13 | 1 |
| 14 | 12 | 10 | 2 | 14 | 3 |
| 15 | 13 | 15 | 1 | 15 | 1 |
| 16 | 17 | 22 | 4 | 16 | 3 |
| 17 | 15 | 15 | 2 | 17 | 4 |
| 18 | 20 | 22 | 3 | 18 | 3 |
| 19 | 12 | 14 | 2 | 19 | 3 |
| 20 | 11 | 12 | 2 | 20 | 4 |
| 21 | 6 | 8 | 1 | 21 | 3 |
| 22 | 12 | 15 | 2 | 22 | 3 |
| 23 | 10 | 17 | 3 | 23 | 3 |
| 24 | 13 | 17 | 2 | 24 | 3 |
| 25 | 14 | 15 | 3 | 25 | 3 |
| 26 | 16 | 20 | 2 | 26 | 3 |
| 27 | 11 | 12 | 1 | 27 | 2 |
| 28 | 10 | 10 | 1 | 28 | 3 |
| 29 | 10 | 12 | 1 | 29 | 2 |
| 30 | 12 | 12 | 1 | 30 | 3 |

Results for Patient 4: From these signal counts the average TOP2A/cell, HER2/cell, CEP 17/cell, and 1q25/cell were calculated to be 11.8, 13.8, 1.9, and 2.6, respectively, providing a value of 6.3 TOP2A/CEP 17 EP 17 and 7.4 HER2/CEP 17 for this specimen. Since HER2 is amplified (HER2/CEP 17≦2.0) the patient is a potential candidate for trastuzumab therapy, however, since TOP2A is amplified also (TOP2A/CEP 17≧2.0), and 1q25 is normal (1q25/cell<3.0 and ≧1.5) the patient is less likely to respond to treatment than patients for which TOP2A is not amplified and 1q25 is abnormal, and alternative treatments should be considered. Patient 4 was treated with trastuzumab and showed progressive disease by RECIST criteria.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below.

What is claimed is:

1. A method for identifying a candidate patient for treatment with trastuzumab, the method comprising:
   (a) obtaining a biological sample comprising at least one breast cancer cell from the patient;
   (b) contacting the biological sample with a set of two or more chromosomal probes under conditions sufficient to enable hybridization of the probes to chromosomes in the sample, if any, wherein the probes are able to detect at least the copy numbers for HER-2/neu and the locus TOP2A in the at least one breast cancer cell and contacting the biological sample with one or more corresponding chromosome enumeration probes under conditions sufficient to enable hybridization of the one or more chromosome enumeration probes to chromosomes in the sample, if any; and
   c) identifying the candidate as being suitable for treatment with trastuzumab based on detecting an increase in copy number for HER-2 /neu but no increase in copy number for TOP2A in the sample relative to the one or more chromosome enumeration probes and identifying the candidate as being unsuitable for treatment with trastuzumab based on detecting an increase in copy number for HER-2/neu and an increase in copy number for TOP2A in the sample relative to the one or more chromosome enumeration probes.

2. The method of claim 1, wherein a) the set of chromosomal probes comprise probes specific for HER-2/neu and specific for TOP2A and said probes are able to detect the copy number for HER-2/neu and specific for TOP2A and b) the one or more chromosome enumeration probes are able to detect the copy number of Chromosome 17.

3. The method of claim 1, wherein the candidate is identified as being suitable for treatment with trastuzumab based on detecting amplification for HER-2/neu but no amplification for TOP2A in the sample.

4. The method of claim 1, wherein in step (c), the detecting an increase in copy number for HER-2/neu and an increase in copy number for TOP2A in the sample relative to the one or more chromosome enumeration probes comprises analysis of at least 20 cells in the sample.

* * * * *